United States Patent
Lee et al.

(10) Patent No.: US 10,383,599 B2
(45) Date of Patent: Aug. 20, 2019

(54) ULTRASOUND DIAGNOSTIC APPARATUS, OPERATING METHOD THEREOF, AND COMPUTER-READABLE RECORDING MEDIUM

(71) Applicant: SAMSUNG MEDISON CO., LTD., Hongcheon-gun (KR)

(72) Inventors: Jin-yong Lee, Hongcheon-gun (KR); Sung-wook Park, Hongcheon-gun (KR); Jin-ki Park, Hongcheon-gun (KR); Joo-hyun Song, Hongcheon-gun (KR); Bong-heon Lee, Hongcheon-gun (KR); Hyuk-Jae Chang, Seoul (KR); Namsik Chung, Seoul (KR); Geu-ru Hong, Seoul (KR); Hyun-joo Kim, Seoul (KR); Chi-young Shim, Seoul (KR)

(73) Assignee: SAMSUNG MEDISON CO., LTD., Hongcheon-gun (KR)

( * ) Notice: Subject to any disclaimer, the term of this patent is extended or adjusted under 35 U.S.C. 154(b) by 952 days.

(21) Appl. No.: 14/938,080

(22) Filed: Nov. 11, 2015

(65) Prior Publication Data

US 2016/0151048 A1 Jun. 2, 2016

(30) Foreign Application Priority Data

Nov. 11, 2014 (KR) .................... 10-2014-0156240

(51) Int. Cl.
*A61B 8/00* (2006.01)
*A61B 8/08* (2006.01)

(52) U.S. Cl.
CPC .............. *A61B 8/469* (2013.01); *A61B 8/461* (2013.01); *A61B 8/465* (2013.01); *A61B 8/466* (2013.01);
(Continued)

(58) Field of Classification Search
CPC ................................ A61B 8/466; A63B 8/469
See application file for complete search history.

(56) References Cited

U.S. PATENT DOCUMENTS

| | | | |
|---|---|---|---|
| 7,433,504 | B2 | 10/2008 | Deischinger et al. |
| 8,591,420 | B2 | 11/2013 | Hamada |

(Continued)

FOREIGN PATENT DOCUMENTS

| | | |
|---|---|---|
| EP | 1967867 A2 | 9/2008 |
| EP | 2335596 A1 | 6/2011 |

(Continued)

OTHER PUBLICATIONS

Communication dated Apr. 4, 2016, from the European Patent Office in counterpart European Application No. 15178315.6.

*Primary Examiner* — Omkar A Deodhar
(74) *Attorney, Agent, or Firm* — Sughrue Mion, PLLC

(57) ABSTRACT

Disclosed are an ultrasound diagnostic apparatus and an operating method thereof, which quickly and accurately set a volume of interest (VOI). The ultrasound diagnostic apparatus includes a data acquiring unit that acquires three-dimensional (3D) ultrasound data about an object, a display unit that displays a plane image of at least one of a plurality of planes included in the object, based on the 3D ultrasound data, a user input unit that receives a user input which sets a first straight line included in the plane image, a VOI setting unit that sets, as a VOI, a volume between a first flat surface, which is parallel to the first straight line and is separated from the first straight line by a first distance, and a second flat surface which is parallel to the first straight line and is separated from the first straight line by a second distance; and an image generating unit that generates at least one selected from a 3D image and a two-dimensional (2D) plane image of the set VOI, based on the 3D ultrasound data. The (Continued)

display unit displays at least one selected from the 3D image and the 2D plane image of the VOI.

17 Claims, 9 Drawing Sheets

(52) U.S. Cl.
CPC .............. *A61B 8/467* (2013.01); *A61B 8/483* (2013.01); *A61B 8/523* (2013.01); *A61B 8/0883* (2013.01)

(56) References Cited

U.S. PATENT DOCUMENTS

| | | | |
|---|---|---|---|
| 8,600,129 B2 | 12/2013 | Seko et al. | |
| 2007/0255136 A1* | 11/2007 | Kristofferson | ........... A61B 8/06 |
| | | | 600/437 |
| 2008/0154952 A1* | 6/2008 | Waldinger | .............. G06T 19/00 |
| 2011/0255762 A1 | 10/2011 | Deischinger et al. | |
| 2014/0184587 A1 | 7/2014 | Park et al. | |

FOREIGN PATENT DOCUMENTS

| | | |
|---|---|---|
| JP | 2006-061698 A | 3/2006 |
| JP | 2008-178662 A | 8/2008 |
| JP | 2011-083439 A | 4/2011 |
| JP | 2012-40207 A | 3/2012 |
| KR | 10-2014-0089049 A | 7/2014 |
| WO | 2004/029655 A1 | 4/2004 |

* cited by examiner

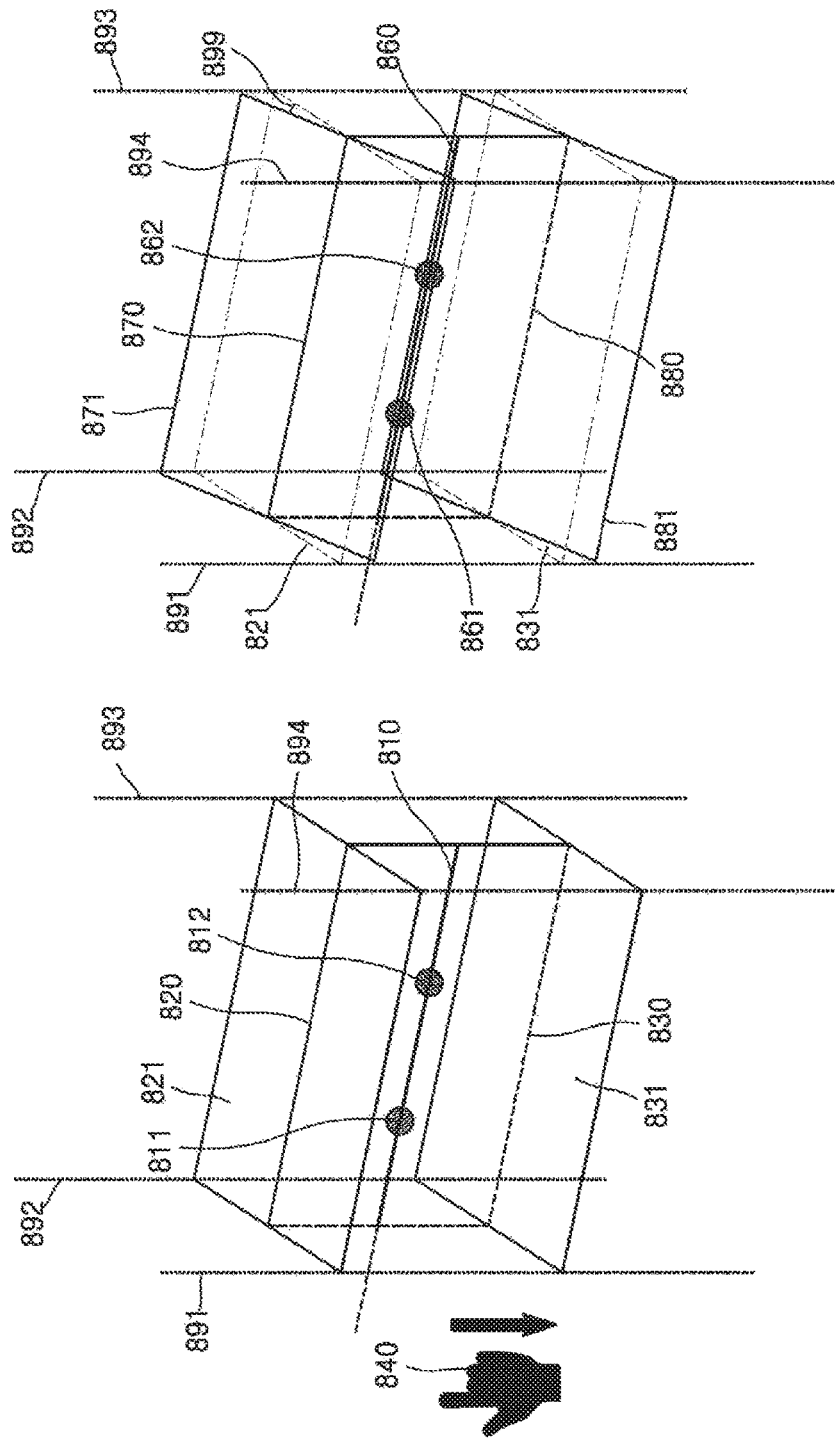

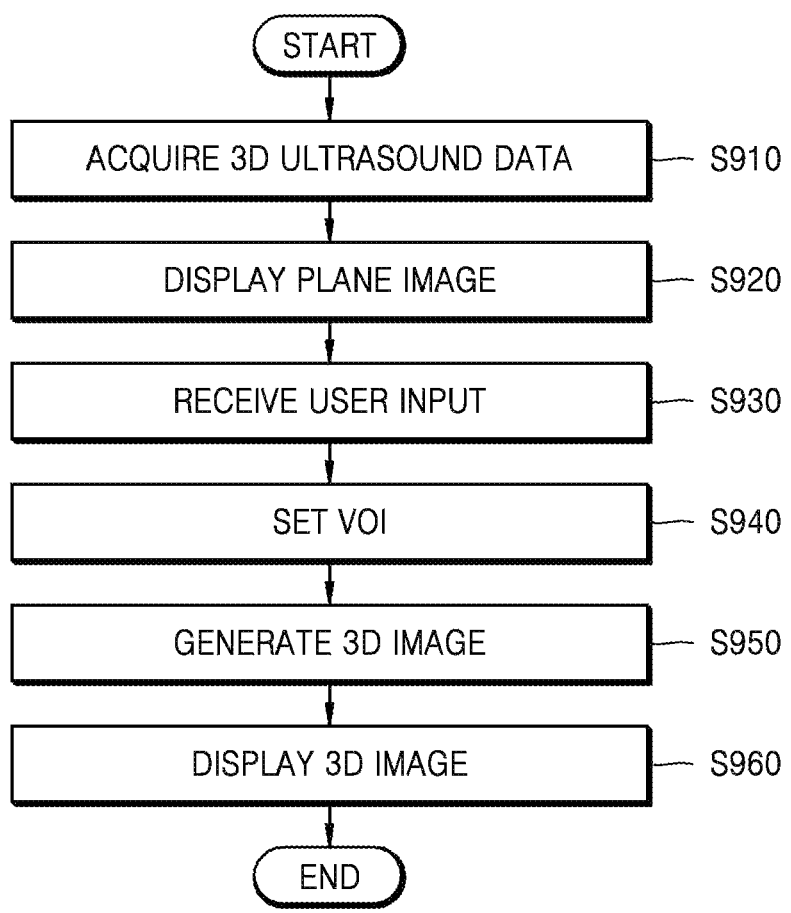

ULTRASOUND DIAGNOSTIC APPARATUS, OPERATING METHOD THEREOF, AND COMPUTER-READABLE RECORDING MEDIUM

CROSS-REFERENCE TO RELATED APPLICATION

This application claims the benefit of Korean Patent Application No. 10-2014-0156240, filed on Nov. 11, 2014, in the Korean Intellectual Property Office, the disclosure of which is incorporated herein in its entirety by reference.

BACKGROUND

1. Field

One or more exemplary embodiments relate to an ultrasound diagnostic apparatus, an operating method thereof, and a computer-readable storage medium, and more particularly, to an ultrasound diagnostic apparatus, an operating method thereof, and a computer-readable recording medium, which enable a volume of interest (VOI), which is to be observed by a user, to be more easily designated in an object during ultrasound diagnosis.

2. Description of the Related Art

Ultrasound diagnostic apparatuses irradiate an ultrasound signal, generated from a transducer of a probe, onto an object and receive information of an echo signal reflected from the object, thereby obtaining an image of an internal part of the object. In particular, ultrasound diagnostic apparatuses are used for the medical purposes of observing the inside of an object, detecting a foreign material, and assessing an injury. Ultrasound diagnostic apparatuses have stabilities higher than those of diagnostic apparatuses using X-rays, display images in real time, and are safe because there is no exposure to radioactivity, and thus may be widely used along with other image diagnostic apparatuses.

In this context, due to advancements in imaging technology, the demand for three-dimensional observation of an object is increasing.

However, in the related art, a minimum of three planes are selected in setting a three-dimensional (3D) VOI. For example, in a method of the related art, one plane is selected in a front view, one plane is selected in a side view, one plane is selected in a plan view, and a rectangular parallelepiped composed of three of the planes is set as a VOI. Such a method is intuitive, but since a VOI having a complicated shape is set, much time is expended. Also, various methods of selecting a VOI without selecting three planes have been proposed, but they cannot accurately set a VOI which is to be observed by a user.

Therefore, an ultrasound diagnostic apparatus and an operating method thereof which quickly and accurately set a VOI are needed.

SUMMARY

One or more exemplary embodiments include an ultrasound diagnostic apparatus and an operating method thereof, which quickly and accurately set a VOI in a 3D ultrasound image.

Additional aspects will be set forth in part in the description which follows and, in part, will be apparent from the description, or may be learned by practice of the presented exemplary embodiments.

According to one or more exemplary embodiments, an ultrasound diagnostic apparatus includes: a data acquiring unit that acquires three-dimensional (3D) ultrasound data about an object; a display unit that displays a plane image of at least one of a plurality of planes included in the object, based on the 3D ultrasound data; a user input unit that receives a user input which sets a first straight line included in the plane image; a VOI setting unit that sets, as a volume of interest (VOI), a volume between a first flat surface, which is parallel to the first straight line and is separated from the first straight line by a first distance, and a second flat surface which is parallel to the first straight line and is separated from the first straight line by a second distance; and an image generating unit that generates at least one selected from a 3D image and a two-dimensional (2D) plane image of the set VOI, based on the 3D ultrasound data, wherein the display unit displays at least one selected from the 3D image and the 2D plane image of the VOI.

The VOI setting unit may set the first flat surface and the second flat surface so that the first flat surface is parallel to the second flat surface.

The VOI setting unit may set the first flat surface for the first flat surface to be vertical to the plane image and set the second flat surface for the second flat surface to be vertical to the plane image.

The user input unit may receive an input which selects a first point and a second point in the plane image, and the first straight line may be a straight line which connects the first point to the second point.

The VOI setting unit may acquire a second straight line and a third straight line which are parallel to the first straight line, so that the first straight line is disposed between the second straight line and the third straight line, acquire the first flat surface including the second straight line, and acquire the second flat surface including the third straight line.

The user input unit may receive an input which selects a third point in the plane image, and the VOI setting unit may set the first flat surface for the first flat surface to include the third point.

The user input unit may receive an input which selects a fourth point in the plane image, and the VOI setting unit may set the second flat surface for the second flat surface to include the fourth point.

The user input unit may receive a second user input which rotates or moves at least one selected from the first flat surface and the second flat surface, and the VOI setting unit may set an angle between a horizontal plane and at least one selected from the first flat surface and the second flat surface or set a distance between the first straight line and at least one selected from the first flat surface and the second flat surface, based on the second user input.

The user input unit may receive a second user input which rotates or moves at least one selected from the first flat surface and the second flat surface, and the VOI setting unit may set the first flat surface to be rotated about the second straight line and set the second flat surface to be rotated about the third straight line, based on the second user input.

According to one or more exemplary embodiments, an operating method of an ultrasound diagnostic apparatus includes: acquiring three-dimensional (3D) ultrasound data about an object; displaying a plane image of at least one of a plurality of planes included in the object, based on the 3D ultrasound data; receiving a user input which sets a first straight line included in the plane image; setting, as a volume of interest (VOI), a volume between a first flat surface, which is parallel to the first straight line and is separated from the first straight line by a first distance, and a second flat surface which is parallel to the first straight line and is separated from the first straight line by a second distance; and generating at least one selected from a 3D image and a two-dimensional (2D) plane image of the set VOI, based on the 3D ultrasound data, wherein the displaying includes displaying at least one selected from the 3D image and the 2D plane image of the VOI.

The setting of the volume may include setting the first flat surface and the second flat surface so that the first flat surface is parallel to the second flat surface.

The setting of the volume may include: setting the first flat surface for the first flat surface to be vertical to the plane image; and setting the second flat surface for the second flat surface to be vertical to the plane image.

The receiving of the user input may include receiving an input which selects a first point and a second point in the plane image, and the first straight line may be a straight line which connects the first point to the second point.

The setting of the volume may include: acquiring a second straight line and a third straight line which are parallel to the first straight line, so that the first straight line is disposed between the second straight line and the third straight line; acquiring the first flat surface including the second straight line; and acquiring the second flat surface including the third straight line.

The receiving of the user input may include receiving an input which selects a third point in the plane image, and the setting of the volume may include setting the first flat surface for the first flat surface to include the third point.

The receiving of the user input may include receiving an input which selects a fourth point in the plane image, and the setting of the volume may include setting the second flat surface for the second flat surface to include the fourth point.

The receiving of the user input may include receiving a second user input which rotates or moves at least one selected from the first flat surface and the second flat surface, and the setting of the volume may include setting an angle between a horizontal plane and at least one selected from the first flat surface and the second flat surface or sets a distance between the first straight line and at least one selected from the first flat surface and the second flat surface, based on the second user input.

The receiving of the user input may include receiving a second user input which rotates or moves at least one selected from the first flat surface and the second flat surface, and the setting of the volume may include setting the first flat surface to be rotated about the second straight line and sets the second flat surface to be rotated about the third straight line, based on the second user input.

According to one or more exemplary embodiments, provided is a non-transitory computer-readable storage medium storing a program for executing the operating method.

BRIEF DESCRIPTION OF THE DRAWINGS

These and/or other aspects will become apparent and more readily appreciated from the following description of the exemplary embodiments, taken in conjunction with the accompanying drawings in which:

FIGS. 8A and 8B are diagrams illustrating an operation of correcting a VOI according to an exemplary embodiment; and FIG. 9 is a flowchart illustrating an operating method of an ultrasound diagnostic apparatus according to an exemplary embodiment.

DETAILED DESCRIPTION

Figure 1:
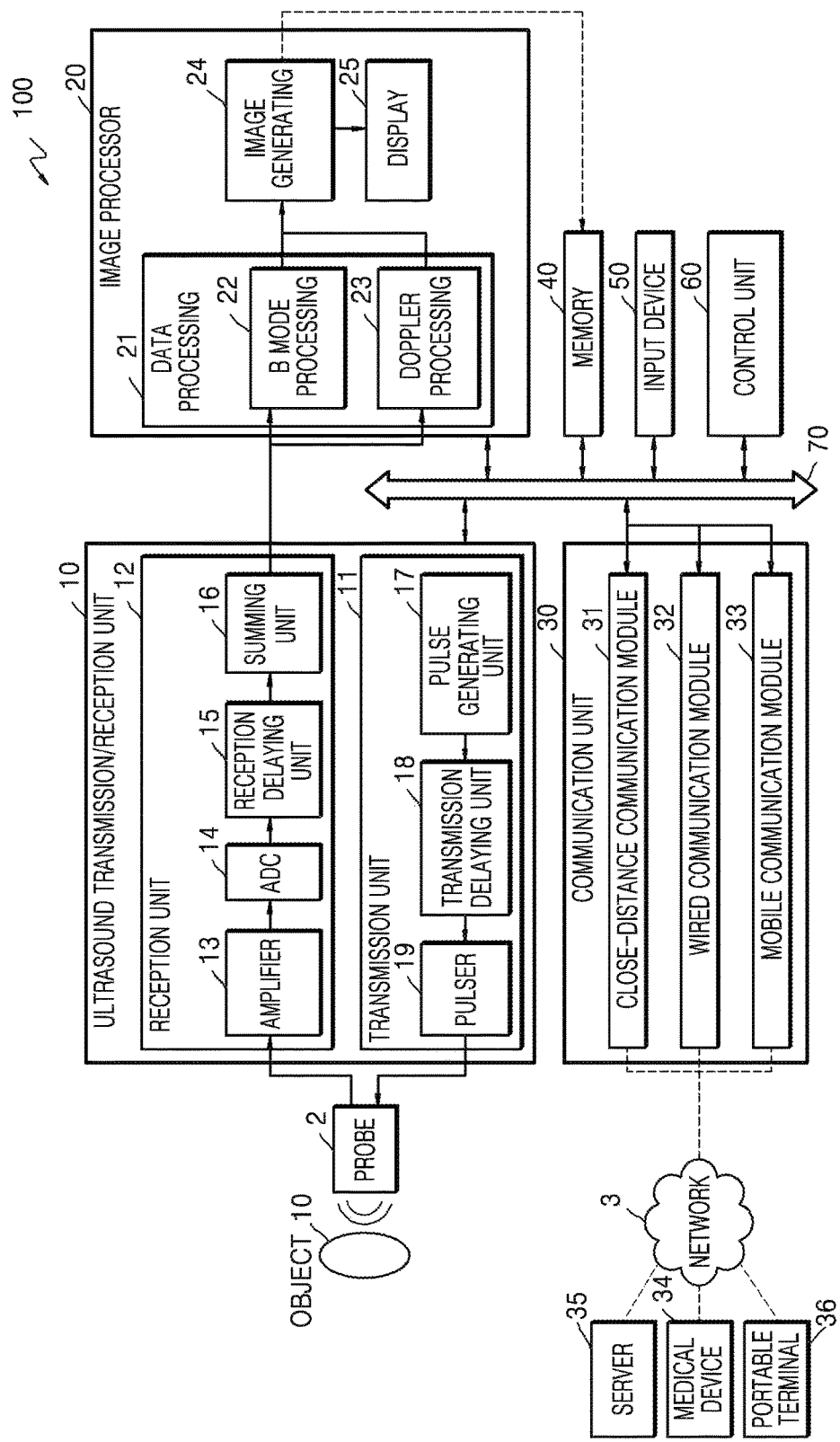
FIG. 1 is a diagram illustrating an ultrasound diagnostic apparatus according to an exemplary embodiment.

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects of the present description.

The terms used in this specification are those general terms currently widely used in the art in consideration of functions regarding the inventive concept, but the terms may vary according to the intention of those of ordinary skill in the art, precedents, or new technology in the art. Also, specified terms may be selected by the applicant, and in this case, the detailed meaning thereof will be described in the detailed description of the invention. Thus, the terms used in the specification should be understood not as simple names but based on the meaning of the terms and the overall description of the invention.

Throughout the specification, it will also be understood that when a component "includes" an element, unless there is another opposite description thereto, it should be understood that the component does not exclude another element and may further include another element. In addition, terms such as " . . . unit", " . . . module", or the like refer to units that perform at least one function or operation, and the units may be implemented as hardware or software or as a combination of hardware and software.

Throughout the specification, an "ultrasound image" refers to an image of an object, which is obtained using ultrasound waves. Furthermore, an "object" may be a human, an animal, or a part of a human or animal. For example, the object may be an organ (e.g., the liver, the heart, the womb, the brain, a breast, or the abdomen), a blood vessel, or a combination thereof. Also, the object may be a phantom. The phantom means a material having a density, an effective atomic number, and a volume that are approximately the same as those of an organism.

Throughout the specification, a "user" may be, but is not limited to, a medical expert, for example, a medical doctor, a nurse, a medical laboratory technologist, or a medical imaging expert, or a technician who repairs medical apparatuses.

Embodiments of the invention now will be described more fully hereinafter with reference to the accompanying drawings, in which illustrative embodiments of the invention are shown.

FIG. 1 is a diagram illustrating an ultrasound imaging apparatus 100 according to exemplary embodiments.

FIG. 1 illustrates an overall configuration of the ultrasound diagnosis apparatus 100 according to exemplary embodiments.

Referring to FIG. 1, the ultrasound diagnosis apparatus 100 may include a probe 2, an ultrasound transceiver 10, an image processor 20, a communication module 30, a display 300, a memory 40, a user input 50, and a controller 60, which may be connected to one another via buses 70.

The ultrasound diagnosis apparatus 100 may be a cart type apparatus or a portable type apparatus. Examples of portable ultrasound diagnosis apparatuses may include, but are not limited to, a picture archiving and communication system (PACS) viewer, a smartphone, a laptop computer, a personal digital assistant (PDA), and a tablet PC.

The probe 2 transmits ultrasound waves to an object 1 in response to a driving signal applied by the ultrasound transceiver 10 and receives echo signals reflected by the object 1. The probe 2 includes a plurality of transducers, and the plurality of transducers oscillate in response to electric signals and generate acoustic energy, that is, ultrasound waves. Furthermore, the probe 2 may be connected to the main body of the ultrasound diagnosis apparatus 100 by wire or wirelessly.

A transmitter 11 supplies a driving signal to the probe 2. The transmitter 1110 includes a pulse generator 17, a transmission delaying unit 18, and a pulser 19. The pulse generator 17 generates pulses for forming transmission ultrasound waves based on a predetermined pulse repetition frequency (PRF), and the transmission delaying unit 18 delays the pulses by delay times necessary for determining transmission directionality. The pulses which have been delayed correspond to a plurality of piezoelectric vibrators included in the probe 2, respectively. The pulser 19 applies a driving signal (or a driving pulse) to the probe 2 based on timing corresponding to each of the pulses which have been delayed.

A receiver 12 generates ultrasound data by processing echo signals received from the probe 2. The receiver 120 may include an amplifier 13, an analog-to-digital converter (ADC) 14, a reception delaying unit 15, and a summing unit 16. The amplifier 13 amplifies echo signals in each channel, and the ADC 14 performs analog-to-digital conversion with respect to the amplified echo signals. The reception delaying unit 15 delays digital echo signals output by the ADC 1124 by delay times necessary for determining reception directionality, and the summing unit 16 generates ultrasound data by summing the echo signals processed by the reception delaying unit 15. In some embodiments, the receiver 12 may not include the amplifier 13. In other words, if the sensitivity of the probe 2 or the capability of the ADC 14 to process bits is enhanced, the amplifier 13 may be omitted.

The image processor 20 generates an ultrasound image by scan-converting ultrasound data generated by the ultrasound transceiver 10 and displays the ultrasound image. The ultrasound image may be not only a grayscale ultrasound image obtained by scanning an object in an amplitude (A) mode, a brightness (B) mode, and a motion (M) mode, but also a Doppler image showing a movement of an object via a Doppler effect. The Doppler image may be a blood flow Doppler image showing flow of blood (also referred to as a color Doppler image), a tissue Doppler image showing a movement of tissue, or a spectral Doppler image showing a moving speed of an object as a waveform.

A B mode processor 22 extracts B mode components from ultrasound data and processes the B mode components. An image generator 24 may generate an ultrasound image indicating signal intensities as brightness based on the extracted B mode components.

Similarly, a Doppler processor 23 may extract Doppler components from ultrasound data, and the image generator 24 may generate a Doppler image indicating a movement of an object as colors or waveforms based on the extracted Doppler components.

The image generator 24 according to an exemplary embodiment may generate at least one selected from a 3D ultrasound image and a two-dimensional (2D) plane image by performing a volume rendering operation on volume data, and may generate an elastography image by imaging a degree of deformation of the object 1 based on a pressure.

Furthermore, the image generator 24 may display various pieces of additional information in an ultrasound image by using text and graphics. In addition, the generated ultrasound image may be stored in the memory 40.

A display 25 displays the generated ultrasound image. The display 25 may display not only an ultrasound image, but also various pieces of information processed by the ultrasound diagnosis apparatus 100 on a screen image via a graphical user interface (GUI). In addition, the ultrasound diagnosis apparatus 100 may include two or more displays 25 according to embodiments.

The communication module 30 is connected to a network 3 by wire or wirelessly to communicate with an external device or a server. The communication module 30 may exchange data with a hospital server or another medical apparatus in a hospital, which is connected thereto via a PACS. Furthermore, the communication module 30 may perform data communication according to the digital imaging and communications in medicine (DICOM) standard.

The communication module 30 may transmit or receive data related to diagnosis of an object, e.g., an ultrasound image, ultrasound data, and Doppler data of the object, via the network 3 and may also transmit or receive medical images captured by another medical apparatus, e.g., a computed tomography (CT) apparatus, a magnetic resonance imaging (MRI) apparatus, or an X-ray apparatus. Furthermore, the communication module 30 may receive information about a diagnosis history or medical treatment schedule of a patient from a server and utilizes the received information to diagnose the patient. Furthermore, the communication module 30 may perform data communication not only with a server or a medical apparatus in a hospital, but also with a portable terminal of a medical doctor or patient.

The communication module 30 is connected to the network 3 by wire or wirelessly to exchange data with a server 35, a medical apparatus 34, or a portable terminal 36. The communication module 30 may include one or more components for communication with external devices. For example, the communication module 1300 may include a local area communication module 31, a wired communication module 32, and a mobile communication module 33.

The local area communication module 31 refers to a module for local area communication within a predetermined distance. Examples of local area communication techniques according to an embodiment may include, but are not limited to, wireless LAN, Wi-Fi, Bluetooth, ZigBee, Wi-Fi Direct (WFD), ultra wideband (UWB), infrared data association (IrDA), Bluetooth low energy (BLE), and near field communication (NFC).

The wired communication module 32 refers to a module for communication using electric signals or optical signals. Examples of wired communication techniques according to an embodiment may include communication via a twisted pair cable, a coaxial cable, an optical fiber cable, and an Ethernet cable.

The mobile communication module 33 transmits or receives wireless signals to or from at least one selected from a base station, an external terminal, and a server on a mobile communication network. The wireless signals may be voice call signals, video call signals, or various types of data for transmission and reception of text/multimedia messages.

The memory 40 stores various data processed by the ultrasound diagnosis apparatus 100. For example, the memory 40 may store medical data related to diagnosis of an object, such as ultrasound data and an ultrasound image that are input or output, and may also store algorithms or programs which are to be executed in the ultrasound diagnosis apparatus 100.

The memory 40 may be any of various storage media, e.g., a flash memory, a hard disk drive, EEPROM, etc. Furthermore, the ultrasound diagnosis apparatus 100 may utilize web storage or a cloud server that performs the storage function of the memory 40 online.

The user input 50 refers to a means via which a user inputs data for controlling the ultrasound diagnosis apparatus 100. The user input 50 may include hardware components, such as a keypad, a mouse, a touch panel, a touch screen, and a jog switch. However, embodiments of the present invention are not limited thereto, and the input device 1600 may further include any of various other input units including an electrocardiogram (ECG) measuring module, a respiration measuring module, a voice recognition sensor, a gesture recognition sensor, a fingerprint recognition sensor, an iris recognition sensor, a depth sensor, a distance sensor, etc.

The controller 60 may control all operations of the ultrasound diagnosis apparatus 100. In other words, the controller 60 may control operations among the probe 2, the ultrasound transceiver 10, the image processor 20, the communication module 30, the memory 40, and the user input 50 shown in FIG. 1.

All or some of the probe 2, the ultrasound transceiver 10, the image processor 20, the communication module 30, the memory 40, the user input 50, and the controller 60 may be implemented as software modules. However, embodiments of the present invention are not limited thereto, and some of the components stated above may be implemented as hardware modules. Furthermore, at least one selected from the ultrasound transceiver 10, the image processor 20, and the communication module 30 may be included in the controller 60. However, embodiments are not limited thereto.

A marker may be set to indicate a predetermined position or set a diagnosis region in an ultrasound image including an object.

In detail, the marker may be set at a portion that is to be observed in detail by the user to diagnose a disease or to check the health of a patient. The inventive concept provides an ultrasound diagnosis apparatus and an ultrasound image display method, which may change and output an ultrasound image to more accurately diagnose an object region in which the marker is set.

Figure 2:
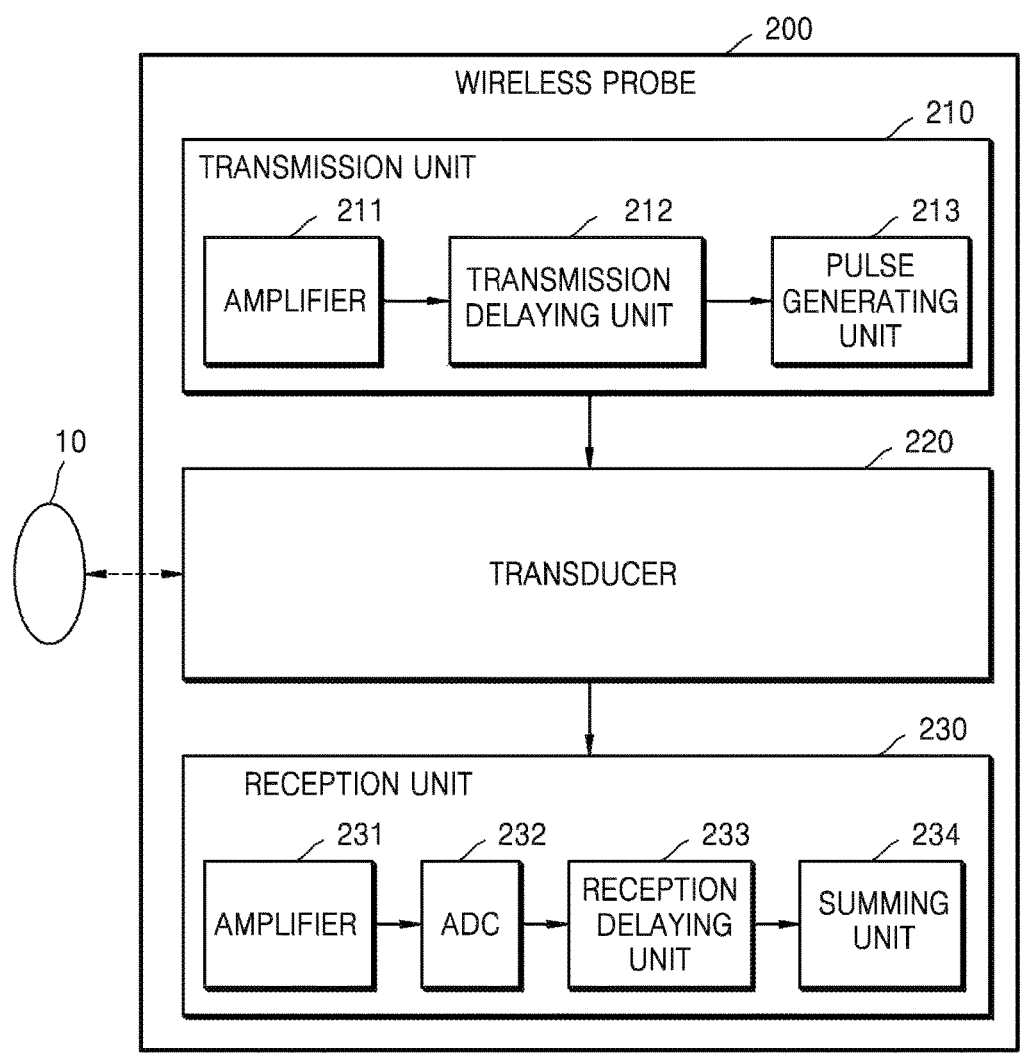
FIG. 2 is a block diagram illustrating a configuration of a wireless probe according to an exemplary embodiment.

FIG. 2 is a block diagram showing a configuration of a wireless probe 200 according to an embodiment of the present invention.

As described above with reference to FIG. 1, the wireless probe 200 may include a plurality of transducers, and, according to embodiments, may include some or all of the components of the ultrasound transceiver 10 shown in FIG. 1.

The wireless probe 200 according to the embodiment shown in FIG. 2 includes a transmitter 210, a transducer 220, and a receiver 230. Since descriptions thereof are given above with reference to FIG. 1, detailed descriptions thereof will be omitted here. In addition, according to embodiments, the wireless probe 200 may selectively include a reception delaying unit 233 and a summing unit 234.

The wireless probe 200 may transmit ultrasound signals to the object 1, receive echo signals from the object 10, generate ultrasound data, and wirelessly transmit the ultrasound data to the ultrasound diagnosis apparatus 100 shown in FIG. 1.

In this context, due to advancements in imaging technology, the demand for three-dimensional observation of an object is increasing. Therefore, an ultrasound diagnostic apparatus and an operating method thereof which quickly and accurately set a VOI are needed.

Hereinafter, an ultrasound diagnostic apparatus, an operating method thereof, and a computer-readable recording medium which quickly and accurately set a VOI, according to exemplary embodiments, will be described in detail with reference to FIGS. 3 to 9.

Figure 3:
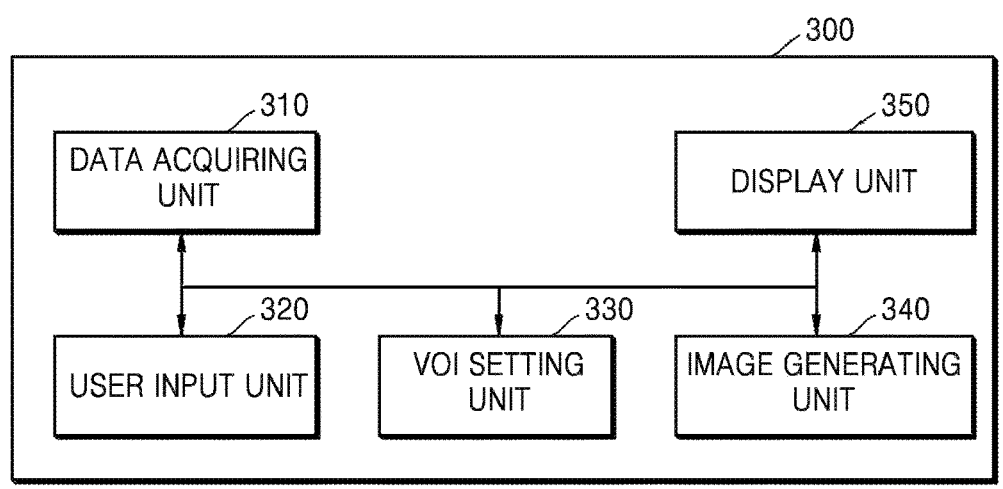
FIG. 3 is a block diagram of an ultrasound diagnostic apparatus according to an exemplary embodiment.

FIG. 3 is a block diagram of an ultrasound diagnostic apparatus 300 according to an exemplary embodiment.

The ultrasound diagnostic apparatus 300 according to an exemplary embodiment includes a data acquiring unit 310, a user input unit 320, a VOI setting unit 330, an image generating unit 340, and a display unit 350.

The data acquiring unit 310 acquires 3D ultrasound data about an object. Also, the data acquiring unit 310 may acquire ultrasound data by using the ultrasound transceiver 10 of FIG. 1. Also, the data acquiring unit 310 may acquire the ultrasound data from at least one selected from the server 35, the medical apparatus 34, and the portable terminal 36 over the network 3 of FIG. 1.

Moreover, the display unit 350 displays one plane image from among planes included in the object, based on the 3D ultrasound data. Also, the display unit 350 displays at least one selected from a 3D image and a 2D plane image of a VOI. Also, the display unit 350 may correspond to the display unit 25 of FIG. 1.

A plane image displayed by the display unit 350 may be a plane image of the object which best represents a part which is to be observed by the user. The plane image may be a plane image representing a plane which is directly set by the user. Alternatively, the plane image may be a plane image representing a plane which is automatically set through image processing by the ultrasound diagnostic apparatus 300. For example, the ultrasound diagnostic apparatus 300 may display a plane image based on a standard view in the display unit 350. The standard view may denote a plane image, which is previously set based on a kind of an object or a disease which is to be diagnosed, among plane images included in the object.

Moreover, the user input unit 320 may receive a user input for setting a first straight line included in the plane image. The user input unit 320 may correspond to the user input unit 50 of FIG. 1. Since the user input unit 50 has been described in detail with reference to FIG. 1, a detailed description on the user input unit 320 will not be provided here.

Moreover, the VOI setting unit 330 may set, as a VOI, a volume between a first flat surface, which is parallel to the first straight line and is separated from the first straight line by a first distance, and a second flat surface which is parallel to the first straight line and is separated from the first straight line by a second distance. The VOI setting unit 330 may be included in the controller 60 of FIG. 1. The VOI setting unit 330 may be implemented by a general-use processor for executing a computer-readable command. However, the present embodiment is not limited thereto.

The VOI denotes a volume region including a certain part of an object which is to be observed by the user. For example, when the user desires to observe a motion of a valve of a heart, a region including the valve in 3D ultrasound data of the heart may be set as the VOI.

The image generating unit 340 generates at least one selected from a 3D image and a 2D plane image of the set VOI, based on the 3D ultrasound data. The image generating unit 340 may correspond to the image generator 24 of FIG. 1. Since the image generator 24 has been described above, a detailed description on the image generating unit 340 is not provided.

Hereinafter, a detailed description on an ultrasound diagnostic apparatus according to an exemplary embodiment will focus on the ultrasound diagnostic apparatus 300 described above with reference to FIG. 3.

Figure 4A:
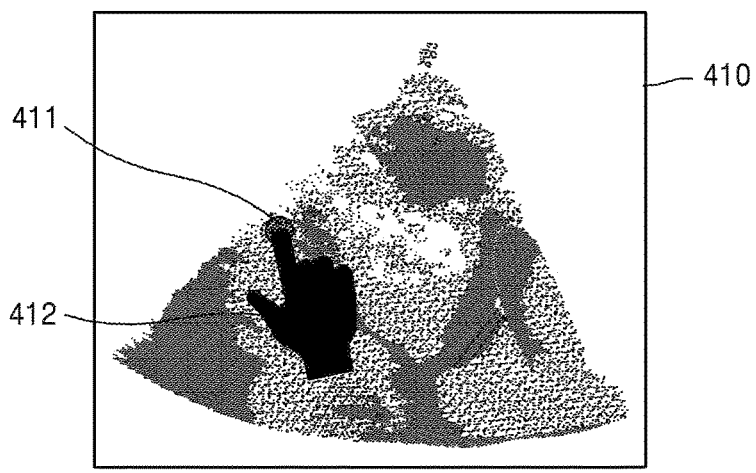
FIGS. 4A, 4B, and 4C are diagrams illustrating an operation of setting a first straight line according to an exemplary embodiment.
Figure 4B:
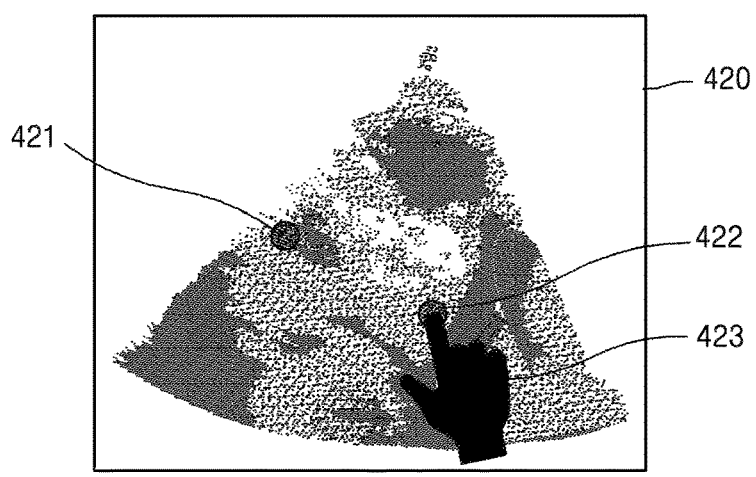
Figure 4C:
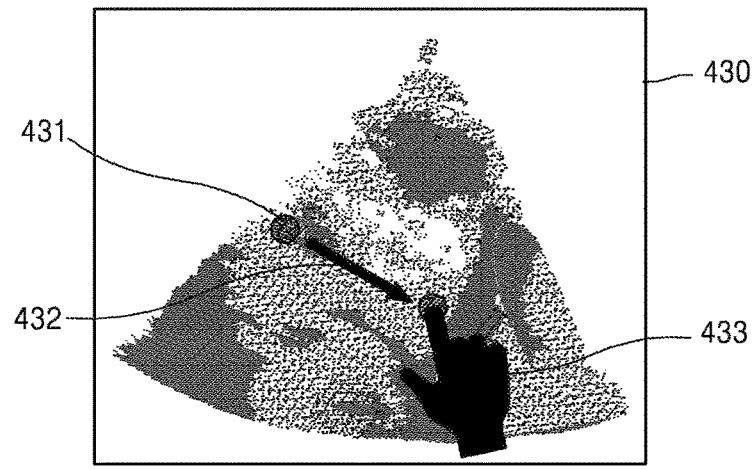

FIGS. 4A, 4B, and 4C are diagrams illustrating an operation of setting a first straight line according to an exemplary embodiment.

The operation of setting the first straight line according to an exemplary embodiment is illustrated in FIG. 4A. Referring to FIG. 4A, the data acquiring unit 310 may acquire 3D ultrasound data about an object. Also, the display unit 350 may display an ultrasound image 430, based on the 3D ultrasound data. The ultrasound diagnostic apparatus 300 may set the first straight line, based on a user input. For example, the user input unit 320 may receive an input, which taps a first point 431 and drags the first point 431 in a certain direction 432, from a user 433. The ultrasound diagnostic apparatus 300 may set the first straight line, based on the received input.

An operation of setting a first straight line according to another exemplary embodiment is illustrated in FIGS. 4B and 4C.

Referring to FIG. 4B, the data acquiring unit 310 may acquire 3D ultrasound data about an object. Also, the display unit 350 may acquire an ultrasound image 410, based on the 3D ultrasound data. The user input unit 320 may receive a first point 411 from a user 412.

Subsequently, referring to FIG. 4C, the user input unit 320 may receive a second point 422 from a user 423. The ultrasound diagnostic apparatus 300 may acquire a straight line, which connects a first point 421 to the second point 422, as a first straight line.

Figure 5A:
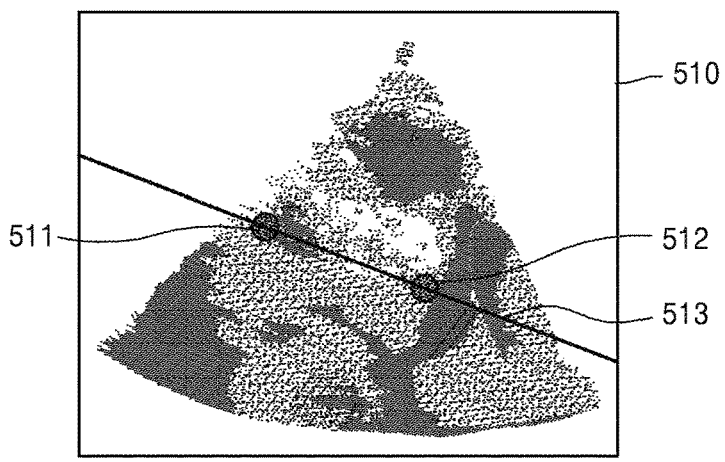
FIGS. 5A, 5B, and 5C are diagrams illustrating an operation of setting a volume of interest (VOI) according to an exemplary embodiment.
Figure 5B:
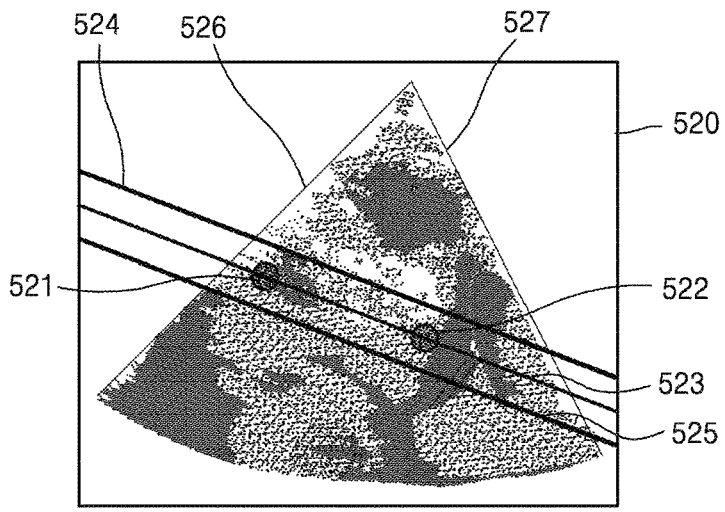
Figure 5C:
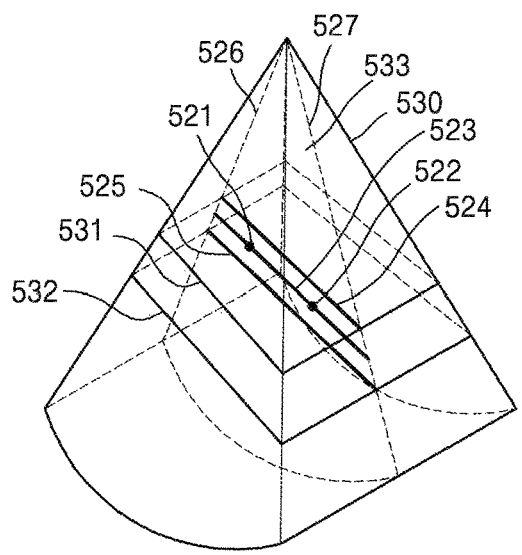

FIGS. 5A, 5B, and 5C are diagrams illustrating an operation of setting a VOI according to an exemplary embodiment.

Referring to FIG. 5A, a first straight line 513 may be acquired through the operation described above with reference to FIG. 4. The display unit 350 may display a first straight line 513 along with an ultrasound image 510. Also, when the first straight line 513 is acquired as illustrated in FIGS. 4B and 4C, the display unit 350 may display a first point 511 and a second point 512.

Referring to FIG. 5C, the first straight line 513 of FIG. 5A corresponds to the first straight line 523 of FIG. 5C. The VOI setting unit 330 may acquire a first flat surface 531 which is parallel to the first straight line 523 and is separated from the first straight line 523 by a first distance. Also, the VOI setting unit 330 may acquire a second flat surface 532 which is parallel to the first straight line 523 and is separated from the first straight line 523 by a second distance. Also, the VOI setting unit 330 may set, as a VOI, a volume between the first flat surface 531 and the second flat surface 532. The ultrasound diagnostic apparatus 300 may automatically set the first distance and the second distance in order for the VOI to be optimally set, based on a kind of an object. Also, the ultrasound diagnostic apparatus 300 may set the first distance and the second distance according to a setting of a user.

The ultrasound diagnostic apparatus 300 may acquire 3D ultrasound data about an object in a region 530. Therefore, the ultrasound diagnostic apparatus 300 may set, as a VOI, a hexahedron formed by a region between the first flat surface 531 and the second flat surface 532 in the region 530.

An operation of setting a VOI according to another exemplary embodiment is illustrated in FIGS. 5A, 5B, and 5C. That is, the first flat surface 531 and the second flat surface 532 may be acquired based on a second straight line 524 and a third straight line 525.

Referring to FIG. 5B, the ultrasound diagnostic apparatus 300 may display an ultrasound image 520 including a plane image of an object. The ultrasound diagnostic apparatus 300 may display the plane image of the object between a boundary 526 and a boundary 527. The VOI setting unit 330 may acquire the second straight line 524 and the third straight line 525 which are parallel to the first straight line 523, so that the first straight line 523 is disposed between the second straight line 524 and the third straight line 525. The VOI setting unit 330 may acquire the second straight line 524 and the third straight line 525 which are separated from the first straight line 523 by a certain distance. The ultrasound diagnostic apparatus 300 may automatically set the certain distance in order for a VOI to be optimally set, based on a kind of the object. Also, the ultrasound diagnostic apparatus 300 may set the certain distance according to a setting of the user.

Moreover, referring to FIG. 5C, the ultrasound diagnostic apparatus 300 may acquire, like the region 530, 3D ultrasound data about the object. An image 533, corresponding to a fan shape illustrated as a dot line including the boundary 526 and the boundary 527, may be a plane image of the object between the boundary 526 and boundary 527 of FIG. 5B. The VOI setting unit 330 may acquire the first flat surface 531 including the second straight line 524 and acquire the second flat surface 532 including the third straight line 525. Also, the VOI setting unit 330 may set, as a VOI, a region between the first flat surface 531 and the second flat surface 532.

The VOI setting unit 330 may set the first flat surface 531 and the second flat surface 532 so that the first flat surface 531 is parallel to the second flat surface 532. Also, the VOI setting unit 330 may set the first flat surface 531 in order for the first flat surface 531 to be vertical to the plane image 533 and set the second flat surface 532 in order for the second flat surface 532 to be vertical to the plane image 533.

Moreover, the image generating unit 340 may generate at least one selected from a 3D image and a 2D plane image of the set VOI, based on the 3D ultrasound data. Also, the display unit 350 may display at least one selected from the 3D image and the 2D plane image of the VOI. The user inputs only the first straight line and thus quickly and accurately sets the VOI.

Figure 6A:
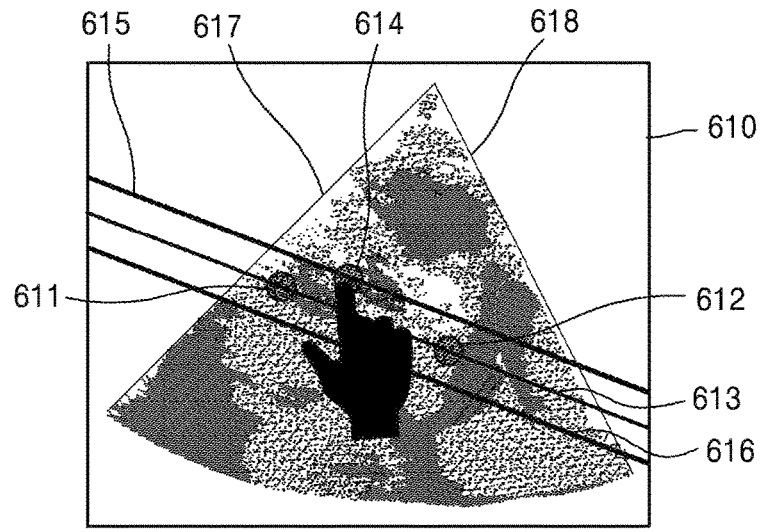
FIGS. 6A and 6B are diagrams illustrating an operation of setting a VOI according to an exemplary embodiment.
Figure 6B:
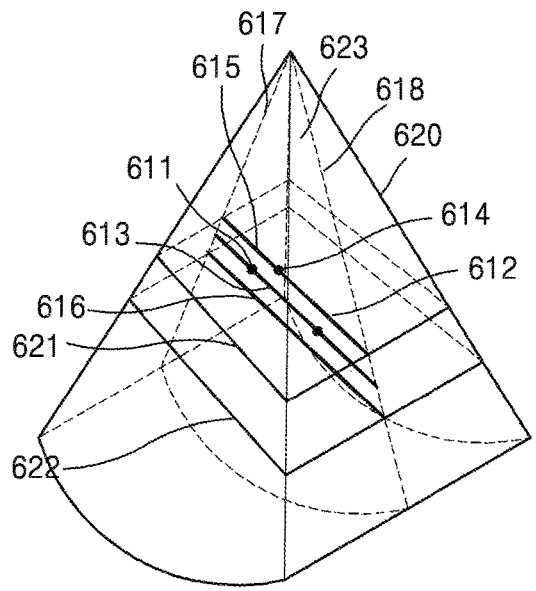

FIGS. 6A and 6B are diagrams illustrating an operation of setting a VOI according to an exemplary embodiment.

The operation of setting the VOI according to an exemplary embodiment will be described below in detail.

Referring to FIG. 6A, a first straight line 613 may be acquired through the operation described above with reference to FIG. 4. The display unit 350 may display the first straight line 613 along with an ultrasound plane image 610. Also, when the first straight line 613 is acquired by the method described above with reference to FIGS. 4B and 4C, the display unit 350 may display a first point 611 and a second point 612. The user input unit 320 may receive an input which selects a third point 614 in a plane image. For example, the third point 614 may be disposed on the first straight line 613 in the ultrasound plane image 610. The display unit 350 may display the third point 614.

Referring to FIG. 6B, the VOI setting unit 330 may set a first flat surface 621 which includes the third point 614 and is parallel to the first straight line 613. Also, the VOI setting unit 330 may set a second flat surface 622 which is parallel to the first straight line 613 and is separated from the first straight line 613 by a second distance. Also, the VOI setting unit 330 may set, as a VOI, a volume between the first flat surface 621 and the second flat surface 622. The ultrasound diagnostic apparatus 300 may automatically set the second distance in order for the VOI to be optimally set, based on a kind of an object. Also, the ultrasound diagnostic apparatus 300 may set the second distance according to a user input. Since the first flat surface 621 includes the third point 614 selected by a user input, the ultrasound diagnostic apparatus 300 may not separately set a distance between the first flat surface 621 and the first straight line 613.

The ultrasound diagnostic apparatus 300 may acquire 3D ultrasound data about an object in a region 620. Therefore, the ultrasound diagnostic apparatus 300 may set, as a VOI, a hexahedron formed by a region between the first flat surface 621 and the second flat surface 622 in the region 620.

An operation of setting a VOI according to another exemplary embodiment is as follows. That is, the first flat surface 621 and the second flat surface 622 may be acquired based on a second straight line 615 and a third straight line 616.

Referring to FIG. 6A, the ultrasound diagnostic apparatus 300 may display an ultrasound image 610 including a plane image of an object. The ultrasound diagnostic apparatus 300 may display the plane image of the object between a boundary 617 and a boundary 618.

The VOI setting unit 330 may set the second straight line 615 which includes the third point 614 and is parallel to the first straight line 613. Also, since the second straight line 615 is disposed on the first straight line 613 in the ultrasound plane image 610, the VOI setting unit 330 may acquire the third straight line 616 which is parallel to the first straight line 613, so that the third straight line 616 is disposed under the first straight line 613. The VOI setting unit 330 may acquire the third straight line 616 which is separated from the first straight line 613 by a certain distance. The ultrasound diagnostic apparatus 300 may automatically set a second distance in order for a VOI to be optimally set, based on a kind of the object. Also, the ultrasound diagnostic apparatus 300 may set the second distance according to a setting of the user.

Moreover, referring to FIG. 6B, the ultrasound diagnostic apparatus 300 may acquire, like the region 620, 3D ultrasound data about the object. An image 623, corresponding to a fan shape illustrated as a dot line including the boundary 617 and the boundary 618, may be a plane image of the object between the boundary 617 and boundary 618 of FIG. 6A. The VOI setting unit 330 may acquire the first flat surface 621 including the second straight line 615 and acquire the second flat surface 622 including the third straight line 616. Also, the VOI setting unit 330 may set, as a VOI, a region between the first flat surface 621 and the second flat surface 622.

Figure 7A:
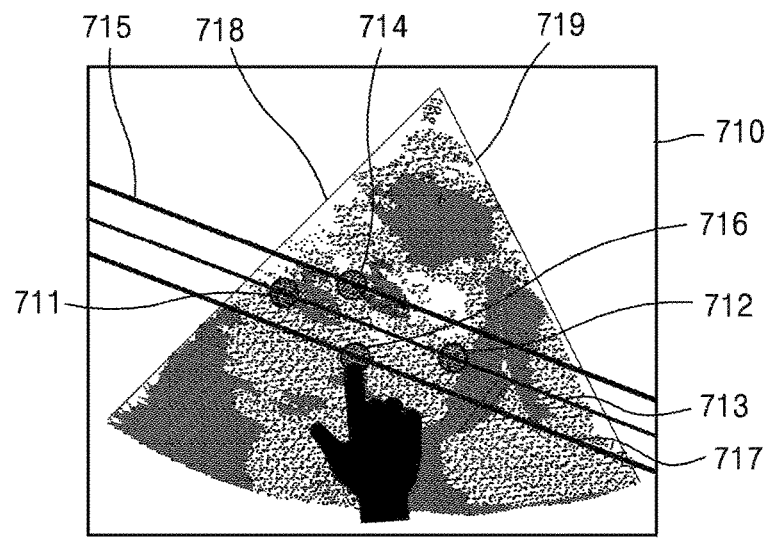
FIGS. 7A and 7B are diagrams illustrating an operation of setting a VOI according to an exemplary embodiment.
Figure 7B:
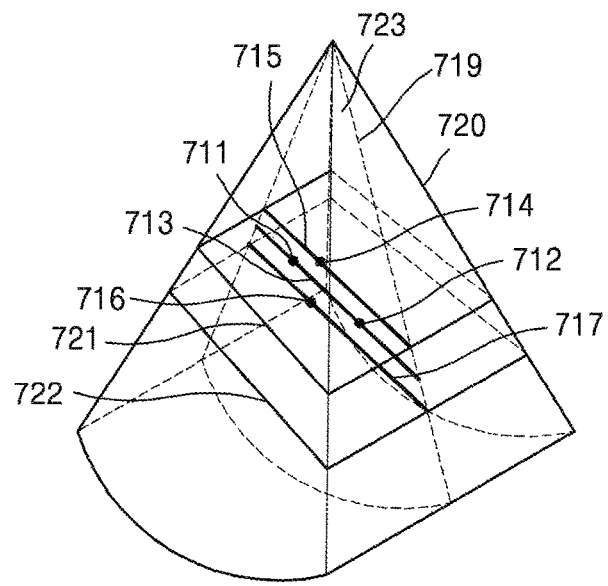

FIGS. 7A and 7B are diagrams illustrating an operation of setting a VOI according to an exemplary embodiment.

The operation of setting the VOI according to an exemplary embodiment will be described below in detail.

Referring to FIG. 7A, a first straight line 713 may be acquired through the operation described above with reference to FIG. 4. The display unit 350 may display the first straight line 713 along with an ultrasound plane image 710. Also, when the first straight line 713 is acquired by the method described above with reference to FIGS. 4B and 4C, the display unit 350 may display a first point 711 and a second point 712. The user input unit 320 may receive an input which selects a third point 714 and a fourth point 716 in a plane image. For example, the third point 714 may be disposed on the first straight line 713 in the ultrasound plane image 710. Also, the fourth point 716 may be disposed under the first straight line 713 in the ultrasound plane image 710. The display unit 350 may display the third point 714 and the fourth point 716.

Referring to FIG. 7B, the VOI setting unit 330 may set a first flat surface 721 which includes the third point 714 and is parallel to the first straight line 713. Also, the VOI setting unit 330 may set a second flat surface 722 which includes the fourth point 716 and is parallel to the first straight line 713. Also, the VOI setting unit 330 may set, as a VOI, a volume between the first flat surface 721 and the second flat surface 722.

The ultrasound diagnostic apparatus 300 may acquire 3D ultrasound data about an object in a region 720. Therefore, the ultrasound diagnostic apparatus 300 may set, as a VOI, a hexahedron formed by a region between the first flat surface 721 and the second flat surface 722 in the region 720.

An operation of setting a VOI according to another exemplary embodiment is as follows. That is, the first flat surface 721 and the second flat surface 722 may be acquired based on a second straight line 715 and a third straight line 717.

Referring to FIG. 7A, the ultrasound diagnostic apparatus 300 may display an ultrasound image 710 including a plane image of an object. The ultrasound diagnostic apparatus 300 may display the plane image of the object between a boundary 718 and a boundary 719.

The VOI setting unit 330 may set the second straight line 715 which includes the third point 714 and is parallel to the first straight line 713. Also, the VOI setting unit 330 may set the third straight line 717 which includes the fourth point 716 and is parallel to the first straight line 713.

Moreover, referring to FIG. 7B, the ultrasound diagnostic apparatus 300 may acquire, like the region 720, 3D ultrasound data about the object. An image 723, corresponding to a fan shape illustrated as a dot line including the boundary 718 and the boundary 719, may be a plane image of the object between the boundary 718 and boundary 719 of FIG. 7A. The VOI setting unit 330 may acquire the first flat surface 721 including the second straight line 715 and acquire the second flat surface 722 including the third straight line 717. Also, the VOI setting unit 330 may set, as a VOI, a region between the first flat surface 721 and the second flat surface 722.

FIGS. 8A and 8B are diagrams illustrating an operation of correcting a VOI according to an exemplary embodiment.

According to an exemplary embodiment, the user input unit 320 may receive a second user input which rotates or moves at least one selected from a first flat surface and a second flat surface. Also, the VOI setting unit 330 may set an angle between a horizontal plane and at least one selected from the first flat surface and the second flat surface, based on the second user input. Also, the VOI setting unit 330 may set a distance between a first straight line and at least one selected from the first flat surface and the second flat surface, based on the second user input.

Moreover, according to another exemplary embodiment, the user input unit 320 may receive the second user input which rotates or moves at least one selected from the first flat surface and the second flat surface. Also, the VOI setting unit 330 may allow the first flat surface to be rotated about a second straight line and allow the second flat surface to be rotated about a third straight line, based on the second user input.

Referring to FIGS. 8A and 8B, the ultrasound diagnostic apparatus 300 may acquire 3D ultrasound data about the inside of a region formed by a plurality of boundaries 891 to 894. The ultrasound diagnostic apparatus 300 may acquire a first straight line 810, based on a received user input. The VOI setting unit 330 may acquire a first flat surface 821 and a second flat surface 831, based on the first straight line 810. The display unit 350 may display the first straight line 810, the first flat surface 821, and the second flat surface 831. Also, according to an operation of acquiring a VOI, the display unit 350 may display a first straight point 811, a second straight point 812, a second straight line 820, and a third straight line 830.

The user input unit 320 may receive, from a user, an input for correcting a VOI. For example, the user input unit 320 may receive an input which taps and downward drags at least one selected from the first flat surface 821 and the second flat surface 822.

Referring to FIG. 8B, the VOI setting unit 330 may set a VOI, based on a user input. For example, the VOI setting unit 330 may correct the first flat surface 821 to a new first flat surface 871, based on a user input. Likewise, the VOI setting unit 330 may correct the second flat surface 831 to a new second flat surface 881. That is, the VOI setting unit 330 may change, by a certain angle 899, a slope of at least one selected from the first flat surface and the second flat surface, based on a user input. Also, unlike the above-described example, a distance from the first and second flat surfaces 871 and 881 to the first straight line 860 may be corrected. The VOI setting unit 330 may acquire, as a VOI, a region formed by the corrected first flat surface 871, the corrected second flat surface 881, and the boundaries 891 to 894.

In detail, according to another exemplary embodiment, the user input unit 320 may receive a user input which rotates or moves at least one selected from the first flat surface 871 and the second flat surface 881. Also, the VOI setting unit 330 may allow the first flat surface 871 to be rotated about a second straight line 870 and allow the second flat surface 881 to be rotated about a third straight line 880, based on the user input. The VOI setting unit 330 may acquire, as a VOI, a region formed by the corrected first flat surface 871, the corrected second flat surface 881, and the boundaries 891 to 894.

FIG. 9 is a flowchart illustrating an operating method of an ultrasound diagnostic apparatus according to an exemplary embodiment.

Referring to FIG. 9, the operating method of the ultrasound diagnostic apparatus according to an exemplary embodiment may include operation S910 of acquiring 3D ultrasound data, operation S920 of displaying a plane image, operation S930 of receiving a user input, operation S940 of setting a VOI, operation S950 of generating at least one selected from a 3D image and a 2D plane image, and operation S960 of displaying at least one selected from the 3D image and the 2D plane image.

In operation S910, the data acquiring unit 310 may acquire 3D ultrasound data about an object.

In operation S920, the display unit 350 may display a plane image of at least one of planes included in the object, based on the 3D ultrasound data. In operation S930, the user input unit 320 may receive a user input which sets a first straight line included in the plane image. In operation S940, the VOI setting unit 330 may set, as a VOI, a volume between a first flat surface, which is parallel to the first straight line and is separated from the first straight line by a first distance, and a second flat surface which is parallel to the first straight line and is separated from the first straight line by a second distance. In operation S950, the image generating unit 340 may generate at least one selected from a 3D image and a 2D plane image of the set VOI, based on the 3D ultrasound data. In operation S960, the display unit 350 may display at least one selected from the 3D image and the 2D plane image of the VOI.

Moreover, referring to FIG. 5A, operation S930 of receiving a user input may include an operation of receiving an input which selects the first point 511 and the second point 512. The user input unit 320 may perform an operation of receiving an input which selects the first point 511 and the second point 512 in the plane image. Also, the ultrasound diagnostic apparatus 300 may acquire a straight line, which connects the first point 511 to the second point 512, as the first straight line 513.

Moreover, referring to FIG. 6A, operation S930 of receiving a user input may include an operation of receiving an input which selects the third point 614 in the plane image. Also, referring to FIG. 7A, operation S930 of receiving a user input may include an operation of receiving an input which selects the fourth point 716 in the plane image. Also, referring to FIG. 8A, operation S930 of receiving a user input may include an operation of receiving a second user input which rotates or moves at least one selected from the first flat surface 821 and the second flat surface 831. Also, referring to FIG. 8B, operation S930 of receiving a user input may include an operation of receiving a second user input which rotates or moves at least one selected from the first flat surface 821 and the second flat surface 831.

The VOI setting unit 330 may perform an operation of setting a first flat surface and a second flat surface so that the first flat surface is parallel to the second flat surface. The VOI setting unit 330 may perform operation S940 of setting a VOI based on the first flat surface and the second flat surface.

The ultrasound diagnostic apparatus 300 may set the first flat surface and the second flat surface so as to be parallel to each other, for providing an optimal VOI to a user. However, the present embodiment is not limited thereto. For example, the first flat surface and the second flat surface may be set so as not to be parallel to each other, based on a preference of a user or a part of an object.

For example, the ultrasound diagnostic apparatus 300 may set the first flat surface in order for the first flat surface to be vertical to a plane image and set the second flat surface in order for the second flat surface to be vertical to the plane image. Also, the VOI setting unit 330 may set the first flat surface in order for the first flat surface to be vertical to the plane image. Also, the VOI setting unit 330 may set the second flat surface in order for the second flat surface to be vertical to the plane image.

Moreover, referring to FIG. 5B, operation S940 of setting a VOI may include an operation which acquires the second straight line 524 and the third straight line 525 which are parallel to the first straight line 523, so that the first straight line 523 is disposed between the second straight line 524 and the third straight line 525. Also, referring to FIG. 5C, operation S940 of setting a VOI may include an operation of acquiring the first flat surface 531 including the second straight line 524 and an operation of acquiring the second flat surface 532 including the third straight line 525.

Moreover, referring to FIG. 6B, operation S940 of setting a VOI may include an operation of acquiring the first flat surface 621 including the third point 614. Also, referring to FIG. 7B, operation S940 of setting a VOI may include an operation of acquiring the second flat surface 722 including the fourth point 716.

Moreover, referring to FIG. 8B, operation S940 of setting a VOI may include an operation which sets an angle between a horizontal plane and at least one selected from the first flat surface 821 and the second flat surface 831, based on the second user input. Also, operation S940 of setting a VOI may include an operation which sets a distance between the first straight line 810 and at least one selected from the first flat surface 821 and the second flat surface 831.

Moreover, operation S940 of setting a VOI may include an operation which sets the first flat surface 821 to be rotated about the second straight line 870 and sets the second flat surface 831 to be rotated about the third straight line 880, based on the second user input.

Moreover, the above-described operating method of the ultrasound diagnostic apparatus may be implemented by a program stored on a non-transitory computer-readable recording medium.

As described above, according to the one or more of the above exemplary embodiments, a user inputs a straight line to a part which is to be observed, thereby quickly setting a VOI. Also, the user inputs a straight line in a length direction of an object, which is to be observed, to set a VOI and thus more accurately sets a VOI. For example, when the user desires to observe a valve of a heart, the user inputs a straight line to near the valve of the heart while checking the display unit of the ultrasound diagnostic apparatus. The ultrasound diagnostic apparatus quickly and accurately sets a VOI, based on the input straight line.

The above-described method may be written as computer programs and may be implemented in general-use digital computers that execute the programs using a non-transitory computer-readable recording medium. Data structures used in the above-described method may be recorded in a non-transitory computer-readable recording medium by using various methods. Examples of the non-transitory computer-readable recording medium include magnetic storage media (e.g., ROM, RAM, USB, floppy disks, hard disks, etc.) and storage media such as optical recording media (e.g., CD-ROMs, or DVDs) and PC interfaces (e.g., PCI, PCI-express, Wi-Fi, etc.).

It should be understood that the exemplary embodiments described herein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope as defined by the following claims.

What is claimed is:

1. An ultrasound diagnostic apparatus comprising:
   a data acquiring unit that acquires three-dimensional (3D) ultrasound data about an object;
   a display that displays a plane image of at least one of a plurality of planes included in the object, based on the 3D ultrasound data;
   a user input interface that receives a user input which sets a first straight line included in the plane image;
   a processor that sets, as a volume of interest (VOI), a volume between a first flat surface, which is parallel to the first straight line and is separated from the first straight line by a first distance, and a second flat surface which is parallel to the first straight line and is separated from the first straight line by a second distance; and
   an image processor that generates at least one selected from a 3D image and a two-dimensional (2D) plane image of the set VOI, based on the 3D ultrasound data,
   wherein the display displays at least one selected from the 3D image and the 2D plane image of the VOI, and
   wherein the processor acquires a second straight line and a third straight line which are parallel to the first straight line, so that the first straight line is disposed between the second straight line and the third straight line, acquires the first flat surface including the second straight line, and acquires the second flat surface including the third straight line.

2. The ultrasound diagnostic apparatus of claim 1, wherein the processor sets the first flat surface and the second flat surface so that the first flat surface is parallel to the second flat surface.

3. The ultrasound diagnostic apparatus of claim 1, wherein the processor sets the first flat surface for the first flat surface to be vertical to the plane image and sets the second flat surface for the second flat surface to be vertical to the plane image.

4. The ultrasound diagnostic apparatus of claim 1, wherein,
   the user input interface receives an input which selects a first point and a second point in the plane image, and
   the first straight line is a straight line which connects the first point to the second point.

5. The ultrasound diagnostic apparatus of claim 4, wherein,
   the user input interface receives an input which selects a third point in the plane image, and
   the processor sets the first flat surface for the first flat surface to include the third point.

6. The ultrasound diagnostic apparatus of claim 5, wherein,
   the user input interface receives an input which selects a fourth point in the plane image, and
   the processor sets the second flat surface for the second flat surface to include the fourth point.

7. The ultrasound diagnostic apparatus of claim 1, wherein,
   the user input interface receives a second user input which rotates or moves at least one selected from the first flat surface and the second flat surface, and
   the processor sets an angle between a horizontal plane and at least one selected from the first flat surface and the second flat surface or sets a distance between the first straight line and at least one selected from the first flat surface and the second flat surface, based on the second user input.

8. The ultrasound diagnostic apparatus of claim 1, wherein,
   the user input interface receives a second user input which rotates or moves at least one selected from the first flat surface and the second flat surface, and the processor sets the first flat surface to be rotated about the second straight line and sets the second flat surface to be rotated about the third straight line, based on the second user input.

9. An operating method of an ultrasound diagnostic apparatus, the operating method comprising:
- acquiring three-dimensional (3D) ultrasound data about an object;
- displaying a plane image of at least one of a plurality of planes included in the object, based on the 3D ultrasound data;
- receiving a user input which sets a first straight line included in the plane image;
- setting, as a volume of interest (VOI), a volume between a first flat surface, which is parallel to the first straight line and is separated from the first straight line by a first distance, and a second flat surface which is parallel to the first straight line and is separated from the first straight line by a second distance; and
- generating at least one selected from a 3D image and a two-dimensional (2D) plane image of the set VOI, based on the 3D ultrasound data,
- wherein the displaying comprises displaying at least one selected from the 3D image and the 2D plane image of the VOI,
- wherein the setting of the volume comprises:
  - acquiring a second straight line and a third straight line which are parallel to the first straight line, so that the first straight line is disposed between the second straight line and the third straight line;
  - acquiring the first flat surface including the second straight line; and
  - acquiring the second flat surface including the third straight line.

10. The operating method of claim 9, wherein the setting of the volume comprises setting the first flat surface and the second flat surface so that the first flat surface is parallel to the second flat surface.

11. The operating method of claim 9, wherein the setting of the volume comprises:
- setting the first flat surface for the first flat surface to be vertical to the plane image; and
- setting the second flat surface for the second flat surface to be vertical to the plane image.

12. The operating method of claim 9, wherein, the receiving of the user input comprises receiving an input which selects a first point and a second point in the plane image, and
the first straight line is a straight line which connects the first point to the second point.

13. The operating method of claim 12, wherein, the receiving of the user input comprises receiving an input which selects a third point in the plane image, and
the setting of the volume comprises setting the first flat surface for the first flat surface to include the third point.

14. The operating method of claim 13, wherein,
the receiving of the user input comprises receiving an input which selects a fourth point in the plane image, and
the setting of the volume comprises setting the second flat surface for the second flat surface to include the fourth point.

15. The operating method of claim 9, wherein,
the receiving of the user input comprises receiving a second user input which rotates or moves at least one selected from the first flat surface and the second flat surface, and
the setting of the volume comprises setting an angle between a horizontal plane and at least one selected from the first flat surface and the second flat surface or sets a distance between the first straight line and at least one selected from the first flat surface and the second flat surface, based on the second user input.

16. The operating method of claim 9, wherein,
the receiving of the user input comprises receiving a second user input which rotates or moves at least one selected from the first flat surface and the second flat surface, and
the setting of the volume comprises setting the first flat surface to be rotated about the second straight line and sets the second flat surface to be rotated about the third straight line, based on the second user input.

17. A non-transitory computer-readable storage medium storing a program for executing the operating method of claim 9.

* * * * *